United States Patent [19]

Kershner et al.

[11] 4,447,656
[45] May 8, 1984

[54] SOLVENT SYSTEM FOR OXIDATIVE COUPLING PROCESS

[75] Inventors: Larry D. Kershner; Leonard R. Thompson; Robert M. Strom, all of Midland, Mich.

[73] Assignee: The Dow Chemical Company, Midland, Mich.

[21] Appl. No.: 469,194

[22] Filed: Feb. 24, 1983

Related U.S. Application Data

[63] Continuation-in-part of Ser. No. 241,970, Mar. 9, 1981, abandoned.

[51] Int. Cl.³ .............................................. C07C 39/15
[52] U.S. Cl. .................................... 568/730; 568/722; 568/733
[58] Field of Search ....................... 568/730, 722, 723

[56] References Cited

U.S. PATENT DOCUMENTS

| 3,555,052 | 1/1971 | Yonemitsu et al. | 568/730 |
| 3,562,338 | 2/1971 | Zaweski | 568/730 |
| 3,631,208 | 12/1971 | Hay | 568/730 |
| 4,086,253 | 4/1978 | Hopper et al. | 568/730 |
| 4,205,187 | 5/1980 | Cardenas et al. | 568/730 |

FOREIGN PATENT DOCUMENTS

536277 10/1931 Fed. Rep. of Germany ...... 568/730

*Primary Examiner*—Werren B. Lone
*Attorney, Agent, or Firm*—Douglas N. Deline

[57] ABSTRACT

Products from the heterogeneously catalyzed oxidative coupling of 2,6-ditertiarybutylphenol are prepared in high yield by the use of an unreactive, non-polar liquid reactive medium.

32 Claims, 1 Drawing Figure

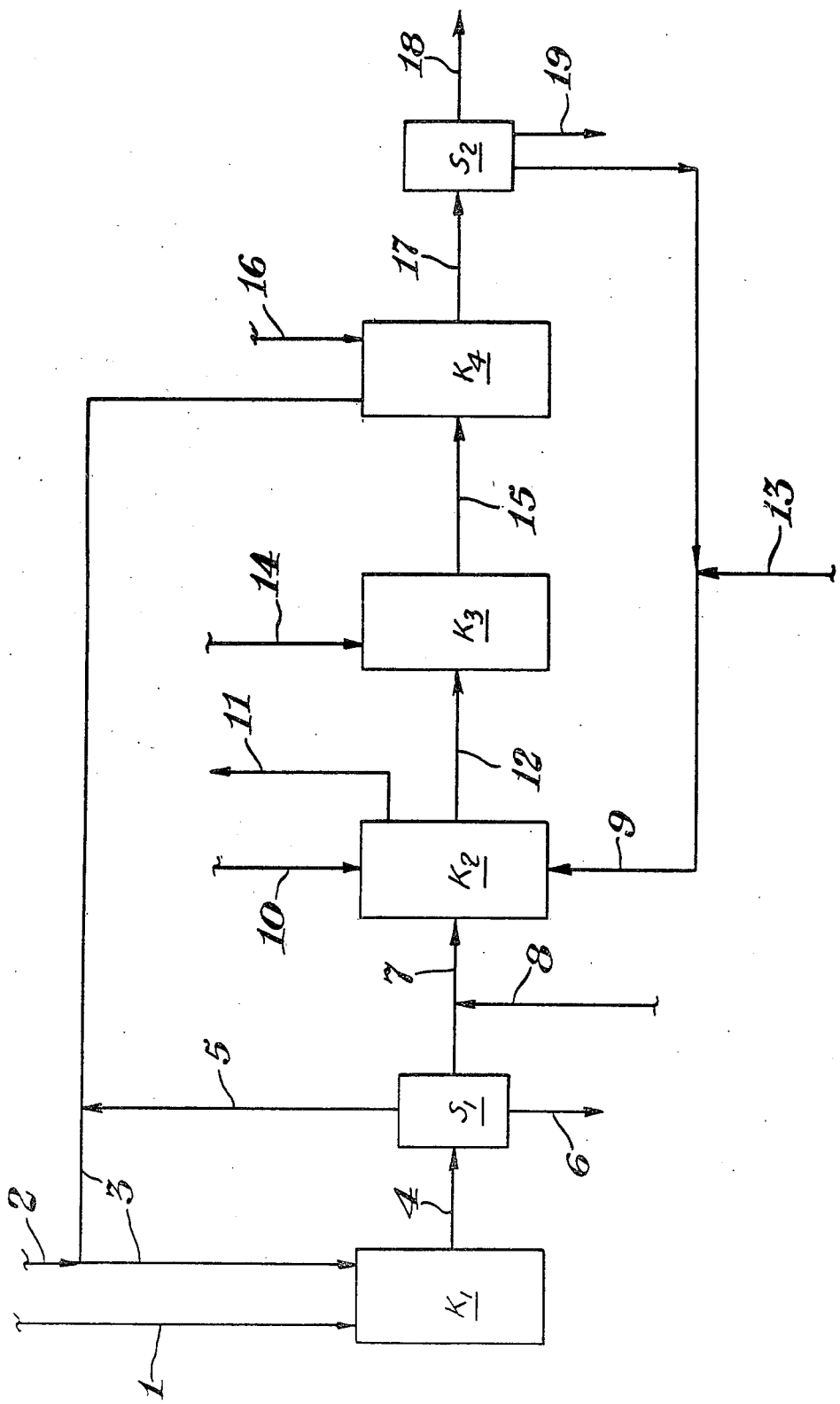

SOLVENT SYSTEM FOR OXIDATIVE COUPLING PROCESS

CROSS-REFERENCE TO RELATED APPLICATION

This is a continuation-in-part of copending application Ser. No. 241,970, filed Mar. 9, 1981 now abandoned.

BACKGROUND OF THE INVENTION

The present invention relates to an improved process for the preparation of 2,2',6,6'-tetratertiary butyl-p,p'-biphenol and p,p'-biphenol by the heterogeneously catalyzed oxidative coupling of phenolic compounds.

Numerous schemes are known in the art to produce self-condensation products by oxidation of phenols. To date, however, a simple process capable of producing 2,2',6,6'-tetratertiarybutyl-p,p'-biphenol and p,p'-biphenol in high yields and selectivities has not been obtained. Generally, prior art processes have been characterized by a low yield of the desired 2,2',6,6'-tetratertiarybutyl-p,p'-biphenol and p,p'-biphenol product, an inability to easily separate the heterogeneous catalyst from the reaction mixture, and poor selectivities toward formation of 2,2',6,6'-tetratertiarybutyl-p,p'-biphenol and p,p'-biphenol reaction product. While heterogeneous catalysts are unexcelled in efficiency in both the oxidative coupling and reduction steps, unless the product can be easily removed for subsequent treatment the greatly increased efficiencies of operation are largely unobtainable to the commercial producer.

We have now found that 2,2',6,6'-tetratertiarybutyl-p,p'-biphenol and p,p'-biphenol may be prepared in high purity and yield and more readily separated and recovered from catalyst and reaction products than heretofore possible.

SUMMARY OF THE INVENTION

The present invention comprises an improved process for formation of 2,2',6,6'-tetratertiarybutyl-p,p'-biphenol and p,p'-biphenol. In simple terms, the process comprises the oxidative coupling of 2,6-ditertiarybutylphenol by contacting the same with a heterogeneous dehydrogenation catalyst under oxidizing conditions in a liquid reaction medium to produce the resulting 3,3',5,5'-tetratertiarybutyl-4,4'-diphenoquinone. Next, the 3,3',5,5'-tetratertiarybutyl-4,4'-diphenoquinone in the same liquid reaction medium is reduced to produce the desired 2,2',6,6'-tetratertiarybutyl-p,p'-biphenol. Finally, in one embodiment of the invention the 2,2',6,6'-tetratertiarybutyl-p,p'-biphenol is dealkylated to produce p,p'-biphenol which is substantially insoluble in the liquid reaction medium employed and easily recovered.

The discovery comprising the heart of the instant invention is that certain liquid mediums may be employed in this process in which 2,6-ditertiarybutylphenol and 2,2',6,6'-tetratertiarybutyl-p,p'-biphenol are both substantially soluble in the liquid reaction medium herein employed thereby allowing for easy separation and recovery of the heterogeneous catalyst. Furthermore, the intermediate product 3,3',5,5'-tetratertiarybutyl -4,4'-diphenoquinone although not necessarily completely soluble in the liquid reaction medium is nevertheless substantially soluble under the reaction conditions employed such that the reduction reaction may proceed to substantial completion in relatively short reaction times. Finally, however, upon dealkylation of the 2,2',6,6'-tetratertiarybutyl-p,p'-biphenol product if desired as an embodiment of the invention, the product, p,p'-biphenol, is substantially insoluble. According to the instant process, the reactants are easily and expeditiously contacted with the respective reactive agents according to the process steps and the heterogeneous catalyst is easily removed after use, but after dealkylation, the dealkylated p,p'-biphenol product is easily separated from the reaction mixture.

DETAILED DESCRIPTION OF THE INVENTION

As previously explained, the unique discovery leading to the instant improved process is in the proper choice of the liquid reaction medium to be employed for the oxidative coupling and subsequent reduction reactions. Such a liquid medium is one wherein 2,6-ditertiarybutylphenol is substantially soluble under the conditions employed in the oxidative coupling reaction and one wherein 2,2',6,6'-tetratertiarybutyl-p,p'-biphenol is additionally substantially soluble under the conditions employed in the oxidative coupling reaction and the reduction reaction, as was previously explained, and additionally, in one embodiment of the invention, one wherein p,p'-biphenol is substantially insoluble under reaction conditions employed for the dealkylation reaction. A suitable medium comprises a relatively nonpolar compound that is substantially unreactive under the reaction conditions employed. Examples include symmetrically halogenated alkanes, e.g., methylene chloride, carbon tetrachloride, etc., and relatively nonpolar aromatic compounds. Especially preferred are high boiling, relatively non-polar aromatic compounds such as dimethylbenzenes, diethylbenzenes, di- and polyhalogenated benzenes such as ortho-dichlorobenzene, tertiary butyl and ditertiary butyl benzenes, diphenyl oxides, etc. Also suitable are mixtures of liquids including mixtures of the above non-polar compounds with small amounts of other unreactive liquids provided that as a whole the liquid reaction medium has the desired properties. By employing a high boiling liquid reaction medium, a subsequent dealkylation reaction if employed, may be accomplished using simple nonpressurized reaction equipment. Preferably, the reaction medium has a boiling point higher than about 180° C. Use of non-halogenated liquids reduces the corrosive effect of the liquid reaction medium at elevated temperatures thereby allowing less costly construction materials to be employed in the reactor equipment design. A preferred liquid reaction medium comprises diethylbenzene.

While not intending to be bound by any particular theory of operation, it is believed the success of the instant invention is explained by the following facts. Both 2,6-ditertiarybutylphenol and 2,2',6,6'-tetratertiarybutyl-p,p'-biphenol contain highly electronegative oxygens bound to an aromatic nucleus. However, because of the environment resulting from the proximity of tertiarybutyl protecting groups on either side of these oxygen moieties, the polar nature of these two compounds is relatively obscured. For this reason both compounds have been found to be soluble in relatively non-polar organic liquids under the reaction conditions herein employed. After dealkylation, however, the electronegative oxygen moiety of the p,p'-biphenol compound is exposed to the environment and renders the compound substantially insoluble in the same relatively non-polar organic liquids. The instant invention results in an efficient method for producing p,p'-biphenol largely because of this difference in solubilities between reactant, intermediate and final product. The same liquid employed to dissolve the beginning and intermediate species under the conditions employed in the reaction readily releases or precipitates the finished compounds, thereby substantially eliminating previously encountered problems in product recovery.

In the operation of the invention, 2,6-ditertiarybutylphenol in a suitable liquid reaction medium as previously defined is admitted to a reactor vessel containing a heterogeneous oxidative coupling catalyst along with an oxygen-containing gas. The oxidative coupling catalysts of the present invention are defined as solids, substantially non-leachable in the reaction medium and capable of producing carbon-carbon coupling products of 2,6-ditertiarybutylphenol under the conditions herein employed. Numerous catalysts have been previously known in the art as suitable oxidative coupling catalysts. Included are the noble metals such as platinum, palladium, ruthenium, rhodium, and iridium present in an oxidative state suitable for catalyzing the oxidative coupling of phenols.

Further suitable heterogeneous oxidative coupling catalysts include the additional members of groups VIII and IB of the Periodic Table along with chromium, molybdenum, zinc or mixtures of the above catalysts. Generally, these catalysts under the conditions of the invention exist in active catalytic species as the corresponding metal oxides.

The catalyst is preferably employed in highly commutated or dispersed form so as to provide as large a surface area as possible for catalytic reaction. The catalyst may be deposited onto a support, preferably one of high surface area in order to produce the desired highly dispersed form. Alternatively, certain of the catalysts, for example, copper chromite, may be treated in known manner to produce a self-supporting porous crystalline catalyst of high surface area.

Isomerization of 2,6-ditertiarybutylphenol to the undesired 2,4-ditertiarybutylphenol has been found to occur under certain reaction conditions. This isomerization may be reduced and even eliminated by employing catalyst supports that are not conducive to such isomerization. Generally therefore, relatively inert supports are preferred as it is believed that the isomerization reaction is promoted by the presence of acids. Additionally, a small amount of a basic compound such as an alkali metal carbonate or hydroxide may be added to reduce this isomerization reaction.

The oxidative coupling reaction is performed at elevated temperatures. Temperatures of from about 30° C. to about 200° C. are operable while temperatures from about 130° C. to about 180° C. are preferred.

As previously explained, an oxygen-containing gas is also present which may be air or oxygen itself. Optionally, the oxygen may be generated in situ. Preferred is to employ a pressurizing gas containing oxygen, as elevated pressures have been found to result in improved reaction rates and yields. Pressures from about atmospheric to about 1000 psig may be employed. Preferred are pressures from 100 to about 500 psig.

The reduction of the 3,3',5,5'-tetratertiarybutyl-4,4'-diphenoquinone to 2,2',6,6'-tetratertiarybutyl-p,p'-biphenol may be accomplished by catalytic reduction in the presence of a heterogeneous reduction catalyst. The step is accomplished under reducing conditions, for example, by contacting the product stream containing 3,3',5,5'-tetratertiarybutyl-4,4'-diphenoquinone in the previously described liquid reaction medium with a heterogeneous reduction catalyst in the presence of a hydrogen-containing gas at elevated temperatures and pressures. Suitable temperatures are from about 25° C. to about 200° C. and preferably about 100° C. to about 160° C. such that the diphenoquinone is retained in solution. Pressures from about atmospheric to about 100 psig may suitably be employed.

The heterogeneous reduction catalysts employed in the reduction operation may be those catalysts corresponding to the oxidative coupling catalysts initially employed, excepting that under the conditions of the reduction, the species responsible for the reaction may differ from the species responsible for the oxidative coupling reaction.

For example, it has been previously stated that in the case of the noble metals, the corresponding noble metal oxide is an effective oxidative coupling catalyst under the conditions herein employed. Under the conditions for reduction in the presence of a hydrogen gas, the active catalytic species is instead the reduced metal.

Copper chromite catalysts are similarly capable of selective hydrogenation or dehydrogenation reactions depending on reaction conditions and catalyst valence. When in a high valence, the catalysts are hydrogenation catalysts. Upon reduction, they become dehydrogenation catalysts. The reduction may occur in situ as, for example, by exposure to the instant reducing medium during the reduction reaction.

Many catalysts contain additional elements intended to stabilize the catalyst. For example, in copper chromite catalysts, barium is sometimes added in order to prevent reduction of the catalyst during hydrogenation reactions.

Included in the invention, however, are all heterogeneous catalysts capable of reducing the 3,3',5,5'-tetratertiarybutyl-4,4'-diphenoquinone to 2,2',6,6'-tetratertiarybutyl-p,p'-biphenol. Preferred are such catalysts containing a metal of Group VIII and IB of the Periodic Table along with chromium, molybdenum and zinc, present in a valence state capable of reducing 3,3',5,5'-tetratertiarybutyl-4,4'-diphenoquinone. The catalyst, however, may contain the aforementioned metals in more than one oxidation state, e.g., as a mixture of the elemental metal and various metal oxides of the same or different metal. The catalysts under the conditions of the reaction are suitably maintained in a valence capable of effecting the catalytic reduction of the diphenoquinone. Most preferred are noble metal-containing catalysts, said noble metal being maintained in a suitable valence.

Alternatively, instead of employing the hydrogen-containing gas in the reduction, high yields of the desired 2,2',6,6'-tetratertiarybutyl-p,p'-biphenol may be produced if the 3,3',5,5'-tetratertiarybutyl-4,4'-diphenoquinone instead is contacted with 2,6-ditertiarybutylphenol.

According to this latter procedure, a solution of 2,6-ditertiarybutylphenol may be partially reacted under the oxidative coupling conditions previously described to about one-half completion or more. At this point, additional 2,6-ditertiarybutylphenol may be added to the reaction mixture such that about 2 moles of 2,6-ditertiarybutylphenol are present for each mole of diphenoquinone. The reaction mixture is thereafter heated until the remaining uncoupled 2,6-ditertiarybutyl phenol and the 3,3',5,5'-tetratertiarybutyl-4,4'-diphenoquinone react together to result in formation of the desired 2,2',6,6'-tetratertiarybutyl-p,p'-biphenol. Oxygen is not employed, however, efforts to substantially exclude oxygen are unnecessary. Hydrogen gas or other reducing agent is not required for the reaction either.

If desired, an additional catalyst may be present in order to aid in effecting the reaction process. Particularly effective are basic catalysts such as amines. Where extra phenol is added to act as reducing agent, the heterogeneous catalyst is generally not catalytically effective for the reduction process.

The invented process includes either of the above-described methods of effecting reduction of the diphenoquinone.

After completion of the reaction, the 2,2',6,6'-tetratertiarybutyl-p,p'-biphenol product may be separated from the liquid reaction mixture after first filtering or otherwise removing the heterogeneous catalyst. The product may be further recovered by removing the liquid reaction medium such as by evaporation or distillation, and used as is or further purified as by recrystallization prior to use as an antioxidant. According to the preferred embodiment of the invention, the 2,2',6,6'-tetratertiarybutyl-p,p'-biphenol is dealkylated to prepare p,p'-biphenol.

One suitable means of accomplishing the dealkylation is to contact the solution of 2,2',6,6'-tetratertiarybutyl-p,p'-biphenol in the liquid reaction medium after first removing the catalyst with a dealkylation agent such as a strong acid, for example, a strong mineral acid or strong organic acid, e.g., p-toluene sulfonic acid. A solid acid such as an acid ion-exchange resin may also be employed. However, this is not preferred since, as previously explained, dealkylation results in precipitation of the desired p,p'-biphenol product. Employing a homogeneous acid, e.g., a liquid, for this dealkylation step, allows for easy separation of precipitated product from the reaction solution.

After dealkylation the liquid reaction medium may be separated from the reaction mixture by decanting or drawing off, and distilled, if desired, to separate acid dealkylation agent. The liquid reaction medium may thereafter be recycled if desired. The product may be recovered and purified by any suitable technique if desired. For example, it has been found that a highly pure product may suitably be prepared by heating the p,p'-biphenol in a modified liquid medium containing a solubilizing agent that renders alkylphenol, isomers other than 4,4'-dihydroxybiphenyl, e.g., 2,2'-dihydroxybiphenyl or 2,4'-dihydroxybiphenyl, and sulfur-containing impurities introduced by the acid catalyst substantially soluble. By the term substantially soluble in this context is meant that the impurities are relatively more soluble in the modified liquid medium than the p,p'-biphenol product such that they may be separated therefrom. Suitable modified liquid mediums are those containing a ketone, alcohol, glycol or caustic solubilizing agent. Especially adapted for subsequent treatment of the p,p'-biphenol product are aqueous solutions of the above solubilizing agents. Accordingly, the crude p,p'-biphenol product is heated in such a modified liquid medium to substantially completely dissolve the above described impurities, if present, and then filtered to yield purified p,p'-biphenol. It is desired that the p,p'-biphenol product remain relatively insoluble in the modified liquid medium.

Alternatively, and most preferably, small amounts of the above solubilizing agent may be present during the course of the present invented process such that at the time of dealkylation the above-described impurities are substantially retained in solution by the liquid reaction medium. Thus, the skilled artisan will recognize that the present invention includes therein the concept of adding small but effective amounts of the above solubilizing agents to the liquid reaction medium either immediately prior to the dealkylation step or at a more preliminary stage. The most advantageous ratio of the various components of the liquid reaction medium may be easily determined by routine optimization of the liquid reaction medium, taking care that the previously described objects and advantages of the present process are not detrimentally effected.

The dealkylation also produces isobutene which is removed from the system as a gas. It is a further embodiment of the invention to recycle the isobutene which may be reacted with phenol in known manner to generate the initial 2,6-ditertiarybutylphenol starting reactant. One such process for producing 2,6-ditertiarybutylphenol employs the reaction of isobutene with aluminum salts of phenol. This process is more fully described in U.S. Pat. No. 2,831,898 which teaching is herein incorporated by reference. Alternatively, the isobutene may be employed in other unrelated industrial processes.

A preferred embodiment of the present invention is illustrated by reference to FIG. 1. The process herein described employs hydrogenation of 3,3',5,5'-tetratertiarybutyl-4,4'-diphenoquinone in the presence of a hydrogen-containing gas and the recycling of isobutene as previously described.

In FIG. 1, phenol is introduced to an alkylation reactor $K_1$ through line 1 where it reacts with isobutene introduced at 2 to line 3. The reaction product containing predominantly 2,6-ditertiarybutylphenol is removed from the reactor through line 4 to a separation zone $S_1$, where unreacted entrained isobutene may be removed and recycled through line 5, and undesired alkylated by-products separated and removed through line 6. Purified 2,6-ditertiarybutylphenol is introduced to reactor $K_2$ containing the heterogeneous dehydrogenation catalyst via line 7. Optionally, additional amounts of 2,6-ditertiarybutylphenol may be admitted via line 8. The liquid medium for the reaction is added from 13 through line 9 while an oxygen-containing gas is admitted through line 10. Water formed during the oxidative coupling reaction is discharged through line 11. Reaction product and solvent are removed through line 12 and charged to reactor $K_3$ which contains a heterogeneous hydrogenation catalyst. A hydrogen-containing gas is admitted to reactor $K_3$ via 14 and the reaction products are removed through line 15 to reactor $K_4$. An acid dealkylation agent is introduced through 16 and isobutylene gas is removed by line 3. The remaining product mixture may be removed via line 17 to a separation zone $S_2$, for separation of product. Solvent is recovered and recycled through line 9. The desired product, p,p'-biphenol, is recovered at 18. Spent acid is removed at 19 and disposed of.

SPECIFIC EMBODIMENTS

Having described our invention, the following examples are provided in further illustration of the inventive features. Applicant's invention, however, is not to be construed as being limited solely to the embodiments disclosed in the following examples.

Example 1—Preparation of 3,3',5,5'-tetratertiarybutyl-4,4'-diphenoquinone 2,6-Ditertiarybutylphenol (100 g) was added to a 600-ml nickel pressure reactor equipped with heating mantle and mechanical stirrer containing 200 ml of diethylbenzene. A 5 percent palladium-on-carbon catalyst (5 g) available commercially from Engelhard Minerals and Chemicals Corp. was added. Analysis of the catalyst surface by Electron Spectroscopy for Chemical Analysis (ESCA) indicated the surface consisted of palladium oxide. The catalyst was not reduced before addition to the reactor. The reactor was sealed and the contents pressurized with oxygen to 250 psig. Stirring was commenced and the reactor was heated to about 100° C. and maintained at that temperature for 1 hour.

Example 2—Preparation of 2,2',6,6'-tetratertiarybutyl-p,p'-biphenol

The reaction process of Example 1 was repeated twice more and the reactor contents of each run were combined in a 2-liter glass round-bottom flask equipped with a gas inlet, mechanical stirrer and a Dean-Stark trap. The flask was purged with nitrogen and heated to 130° C. in order to remove oxygen and by-product water formed by the oxidative coupling reaction. Hydrogen gas was admitted accompanied by stirring until a colorless solution resulted.

Example 3—Preparation of p,p'-biphenol

The reaction mixture of Example 2 was filtered under nitrogen atmosphere to remove catalyst and the clarified filtrate was charged to an additional 2-liter glass flask. p-Toluene sulfonic acid (3 g) was added and the mixture heated accompanied by stirring. The mixture was maintained at 180° C. for about 5 hours. An additional charge of p-toluene sulfonic acid (3 g) was added and heating at 180° C. continued for an additional 12-hour period to insure complete dealkylation.

After cooling to room temperature, a white crystalline solid remained. The product was filtered and washed with additional volumes of diethylbenzene and then dried at 80° C. Analysis by standard analytical techniques demonstrated that the product was substantially pure p,p'-biphenol. Overall yield based on 2,6-ditertiarybutylphenol was 93 percent.

Example 4

The reaction conditions of Examples 1–3 were substantially repeated excepting that the solvent employed was o-dichlorobenzene. Accordingly, 2,6-ditertiarybutylphenol (100 g) was added to 200 ml of o-dichlorobenzene in a 600-ml nickel pressure reactor. The palladium oxide catalyst (5 percent on carbon) was added and the reactor was pressurized under oxygen to 250 psig. The reactor was heated to 70° C. with stirring and maintained at that temperature for 1 hour.

The reaction mixture was then placed into a glass flask equipped with gas inlet, mechanical stirrer and Dean-Stark trap. The flask was purged with nitrogen, then heated to 130° C. and hydrogen was bubbled through the mixture until a colorless solution resulted. Dealkylation was accomplished by addition of 1 g of p-toluene sulfonic acid followed by heating to 180° C. for 5 hours. Analysis of the resulting solution indicated substantially complete conversion of 2,6-ditertiarybutylphenol to p,p'-biphenol had occurred.

What is claimed is:

1. A process for preparation of 2,2',6,6'-tetratertiarybutyl-p,p'-biphenol comprising
   (1) contacting 2,6-ditertiarybutylphenol with an oxygen-containing gas at an elevated temperature and pressure in a liquid reaction medium in the presence of a heterogeneous dehydrogenation catalyst capable of producing carbon-carbon coupling products of the 2,6-ditertiarybutylphenol until substantial amounts of 3,3',5,5'-tetratertiarybutyl-4,4'diphenoquinone are formed;
   (2) reducing the 3,3',5,5'-tetratertiarybutyl-4,4'diphenoquinone by contacting the liquid reaction medium containing 3,3',5,5'-tetratertiarybutyl-4,4'-diphenoquinone under reducing conditions with hydrogen in the presence of a heterogeneous hydrogenation catalyst or with 2,6-ditertiarybutylphenol until substantial amounts of 2,2',6,6'-tetratertiarybutyl-p,p'-biphenol are formed; and
   (3) separating the liquid reaction medium containing 2,2',6,6'-tetratertiarybutyl-p,p'-biphenol from the reaction mixture, provided that the liquid reaction medium is characterized in that under the reaction conditions of steps (1) and (2), 2,6-ditertiarybutylphenol and 3,3',5,5'-tetratertiarybutyl-4,4'-diphenoquinone are substantially soluble; and that under the reaction conditions of steps (2) and (3) 2,2',6,6'-tetratertiarybutyl-p,p'-biphenol is substantially soluble.

2. A process according to claim 1 wherein the liquid reaction medium comprises an unreactive non-polar liquid under the reaction conditions employed.

3. A process according to claim 2 wherein the liquid reaction medium comprises a non-polar aromatic compound.

4. A process according to claim 3 wherein the liquid reaction medium comprises diethylbenzene.

5. A process according to claim 1 wherein in the oxidative coupling reaction, the 2,6-ditertiarybutylphenol is contacted with an oxygen-containing gas in the presence of a heterogeneous dehydrogenation catalyst at a temperature from about 30° C. to about 200° C. at elevated pressure.

6. A process according to claim 5 wherein the oxidative coupling reaction is conducted at a temperature of from about 130° C. to about 180° C. and a pressure from about 100 to about 500 psig.

7. A process according to claim 5 wherein the heterogeneous dehydrogenation catalyst includes a metal of Groups VIII or IB of the Periodic Table, chromium, molybdenum, zinc or a mixture thereof, said metal being present in a valence capable of causing carbon-carbon oxidative coupling or 2,6-ditertiarybutylphenol.

8. A process according to claim 7 wherein the heterogeneous dehydrogenation catalyst is a metal oxide.

9. A process according to claim 1 wherein the 3,3',5,5'-tetratertiarybutyl-4,4'-diphenoquinone is reduced by contacting with a hydrogen-containing gas at an elevated temperature and pressure.

10. A process according to claim 9 wherein the temperature is from about 25° C. to about 200° C.

11. A process according to claim 10 wherein the temperature is from about 100° C. to about 160° C. and the pressure is from atmospheric to about 100 psig.

12. A process according to claim 9 wherein the heterogeneous reduction catalyst includes a metal of Groups VIII or IB of the Periodic Table, chromium, manganese, molybdenum, zinc or a mixture thereof, said metal present in a valence capable of causing reduction of 3,3′,5,5′-tetrateritarybutyl-4,4′-diphenoquinone to 2,2′,6,6′-tetratertiarybutyl-p,p′-biphenol.

13. A process according to claim 12 wherein the heterogeneous catalyst comprises a noble metal.

14. A process for preparation of p,p′-biphenol comprising:
  (1) contacting 2,6-ditertiarybutylphenol with an oxygen-containing gas at an elevated temperature and pressure in a liquid reaction medium in the presence of a heterogeneous dehydrogenation catalyst capable of producing carbon-carbon coupling products of the 2,6-ditertiarybutylphenol until substantial amounts of 3,3′,5,5′-tetratertiarybutyl-4,4′-diphenoquinone are formed;
  (2) reducing the 3,3′,5,5′-tetratertiarybutyl-4,4′-diphenoquinone by contacting the liquid reaction medium containing 3,3′,5,5′-tetratertiarybutyl-4,4′-diphenoquinone under reducing conditions with hydrogen in the presence of a heterogeneous hydrogenation catalyst or with 2,6-ditertiarybutylphenol until substantial amounts of 2,2′,6,6′-tetratertiarybutyl-p,p′-biphenol are formed;
  (3) separating the liquid reaction medium containing 2,2′,6,6′-tetratertiarybutyl-p,p′-biphenol from the reaction mixture;
  (4) contacting the liquid reaction medium containing 2,2′,6,6′-tetratertiarybutyl-p,p′-biphenol with an acid dealkylation agent capable of dealkylating the 2,2′,6,6′-tetratertiarybutyl-p,p′-biphenol at elevated temperature until the 2,2′,6,6′-tetratertiarybutyl-p,p′-biphenol is substantially completely dealkylated; and
  (5) recovering the p,p′-biphenol formed by the process, provided that the liquid reaction medium is characterized in that under the reaction conditions of steps (1) and (2), 2,6-ditertiarybutylphenol and 3,3′,5,5′-tetratertiarybutyl-4,4′-diphenoquinone are substantially soluble; that under the reaction conditions of steps (2), (3) and (4), 2,2′,6,6′-tetratertiarybutyl-p,p′-biphenol is substantially soluble; and that under the reaction conditions of step (4), p,p′-biphenol is substantially insoluble.

15. The process of claim 14 wherein the liquid reaction medium at least during step (4) additionally comprises a solubilizing agent such that alkylphenol, 2,2′-dihydroxybiphenyl, 2,4′-dihydroxybiphenyl, and sulfur-containing impurities are substantially soluble in the liquid reaction medium.

16. A process according to claim 14 wherein at least some 2,6-ditertiarybutylphenol employed in the process is formed by the reaction of phenol and isobutene in a preliminary reaction zone and at least some isobutene employed in the formation of 2,6-ditertiarybutylphenol is formed by the dealkylation of 2,2′,6,6′-tetratertiarybutyl-p,p′-biphenol.

17. A process according to claim 14 wherein the liquid reaction medium comprises an unreactive non-polar liquid under the reaction conditions employed.

18. A process according to claim 17 wherein the liquid reaction medium comprises a non-polar, aromatic compound.

19. A process according to claim 18 wherein the liquid reaction medium boils at a temperature above the temperature employed for the dealkylation of step (4).

20. A process according to claim 19 wherein the liquid reaction medium boils at a temperature above about 180° C.

21. A process according to claim 20 wherein the reaction medium is diethylbenzene.

22. A process according to claim 14 wherein in the oxidative coupling reaction, the 2,6-ditertiarybutylphenol is contacted with an oxygen-containing gas in the presence of a heterogeneous dehydrogenation catalyst at a temperature from about 30° C. to about 200° C. at elevated pressure.

23. A process according to claim 22 wherein the oxidative coupling reaction is conducted at a temperature of from about 130° C. to about 180° C. and a pressure from about 100 to about 500 psig.

24. A process according to claim 22 wherein the heterogeneous dehydrogenation catalyst includes a metal of Groups VIII or IB of the Periodic Table, chromium, molybdenum, zinc or a mixture thereof, said metal present in a valence capable of causing carbon-carbon oxidative coupling of 2,6-ditertiarybutylphenol.

25. A process according to claim 24 wherein the heterogeneous dehydrogenation catalyst is a metal oxide.

26. A process according to claim 22 wherein the reduction is performed by contacting the 3,3′,5,5′-tetratertiarybutyl-4,4′-diphenoquinone with a hydrogen-containing gas at an elevated temperature and pressure.

27. A process according to claim 26 wherein the temperature is from about 25° C. to about 200° C.

28. A process according to claim 27 wherein the temperature is from about 100° C. to about 160° C. and the pressure is from atmospheric to about 100 psig.

29. A process according to claim 26 wherein the heterogeneous reduction catalyst includes a metal of Groups VIII or IB of the Periodic Table, chromium, manganese, molybdenum, zinc or a mixture thereof, said metal present in a valence capable of causing reduction of 3,3′,5,5′-tetratertiarybutyl-4,4′-diphenoquinone to 2,2′,6,6′-tetratertiarybutyl-p,p′-biphenol.

30. A process according to claim 29 wherein the heterogeneous catalyst comprises a noble metal.

31. A process according to claim 14 wherein the acid dealkylation agent is homogeneous.

32. A process according to claim 31 wherein the acid dealkylation agent is p-toluene sulfonic acid.

* * * * *